US012594353B2

(12) United States Patent
Lee et al.

(10) Patent No.: US 12,594,353 B2
(45) Date of Patent: Apr. 7, 2026

(54) HVAC SYSTEM INCLUDING STERILIZATION UNIT

(71) Applicants: HYUNDAI MOTOR COMPANY, Seoul (KR); KIA CORPORATION, Seoul (KR)

(72) Inventors: Sang Shin Lee, Suwon-si (KR); Seong Min An, Seoul (KR); Yoon Hyung Lee, Seongnam-si (KR); Byoung Hyun Ji, Goyang-si (KR)

(73) Assignees: HYUNDAI MOTOR COMPANY, Seoul (KR); KIA CORPORATION, Seoul (KR)

( * ) Notice: Subject to any disclaimer, the term of this patent is extended or adjusted under 35 U.S.C. 154(b) by 650 days.

(21) Appl. No.: 17/991,419

(22) Filed: Nov. 21, 2022

(65) Prior Publication Data

US 2023/0181777 A1 Jun. 15, 2023

(30) Foreign Application Priority Data

Dec. 10, 2021 (KR) ........................ 10-2021-0176452

(51) Int. Cl.
*A61L 2/084* (2026.01)
*A61L 9/18* (2006.01)
*B60H 3/00* (2006.01)

(52) U.S. Cl.
CPC ................. *A61L 2/084* (2013.01); *A61L 9/18* (2013.01); *A61L 2209/16* (2013.01); *B60H 3/00* (2013.01)

(58) Field of Classification Search
CPC ........................................................ A61L 9/18
See application file for complete search history.

(56) References Cited

U.S. PATENT DOCUMENTS

2015/0246148 A1* 9/2015 Blechschmidt ........... A61L 9/20
422/4
2018/0311386 A1* 11/2018 Hawkins ................... F21V 7/00
2023/0190980 A1* 6/2023 Filippone ................. A61L 9/20
422/120

FOREIGN PATENT DOCUMENTS

KR 20-0404862 Y 1/2006

* cited by examiner

*Primary Examiner* — Timothy C Cleveland
(74) *Attorney, Agent, or Firm* — MCDONNELL BOEHNEN HULBERT & BERGHOFF LLP

(57) ABSTRACT

An HVAC system including a sterilization unit is provided, wherein in one embodiment the sterilization unit is located within the HVAC system. The sterilization unit includes a housing configured to envelop an outer side surface of the sterilization unit, an irradiation unit located on one side surface of the housing, and reflection units located in the housing so as to face the irradiation unit.

8 Claims, 9 Drawing Sheets

HVAC SYSTEM INCLUDING STERILIZATION UNIT

CROSS REFERENCE TO RELATED APPLICATION

The present application claims priority to Korean Patent Application No. 10-2021-0176452, filed Dec. 10, 2021, the entire contents of which is incorporated herein for all purposes by this reference.

BACKGROUND

Field

The present disclosure relates to a heating, ventilation, and air conditioning (HVAC) system including a sterilization unit and, more practically, may relate to a sterilization unit of an HVAC system, the sterilization unit irradiating an inner side of a housing with a light ray through an irradiation unit and including a plurality of reflective surfaces configured along an inner surface of the housing so as to allow a plurality of reflected light rays to be maintained in the housing for a long time.

Description of the Related Art

Generally, an HVAC system of a vehicle is divided into a ventilation facility and heating and cooling devices. The ventilation facility replaces polluted air in a vehicle with fresh outside air or removes pollutants through a filter in parallel with circulating the air in the vehicle, thereby maintaining the air in the vehicle to be comfortable. Meanwhile, the heating and cooling devices provide a coolant of an engine and a refrigerant of an air conditioner compressor to a heater core and an evaporator of an air conditioning unit, respectively, in the HVAC system, thereby enabling the temperature inside the vehicle to be selectively maintained in winter and summer.

Such an HVAC system creates a more comfortable indoor environment for a driver and passengers by controlling and maintaining an indoor temperature at a desirable temperature. In general, the air conditioning unit of the vehicle includes a blower that sucks an outside air or an indoor air, an evaporator that cools the sucked air with a refrigerant, and a heater core that heats the sucked air with the heat of the coolant, wherein each element is integrated into one structure to constitute the HVAC system.

In such an HVAC system, various foreign substances and dust adhere to the evaporator and heater core, through which the air sucked into the blower passes, as a driving period of the vehicle elapses so that the driver and passengers breathe air contaminated with unpleasant odors and various germs. In particular, in summer when the temperature is high, various bacteria and fungi proliferate vigorously, causing unpleasant odors and various bacteria-causing respiratory diseases. In order to solve this problem, cleaning liquid is sprayed with a sprayer on the inlet side where the outside air and the inside air are sucked by the blower.

The existing solutions as described above may not clean various foreign substances and dust adhering to the evaporator and heater core and also may not sterilize various bacteria and vigorously proliferating molds. Consequently, there is discomfort in that a user has to inject a cleaning solution. Moreover, it is essentially required that a separate configuration for continuous sterilization of bacteria introduced into the air be provided.

The foregoing is intended merely to aid in the understanding of the background of the present disclosure and is not intended to mean that the present disclosure falls within the purview of the related art that is already known to those skilled in the art.

SUMMARY

Accordingly, the present disclosure has been made keeping in mind the above problems occurring in the related art, and an objective of the present disclosure is to provide an HVAC system including a sterilization unit that is located in the HVAC system and executes sterilization of air flowing through the inside of the HVAC system.

In addition, the present disclosure allows a plurality of reflected light rays to be reflected in the sterilization unit through a plurality of reflection units located at the inner side of the sterilization unit, thereby providing sufficient sterilization performance of the flowing air.

In addition, the present disclosure provides the HVAC system capable of minimizing a height or width of the housing and minimizing flow resistance (airflow reduction/noise) by providing a reflective surface including a plurality of parabolic shapes.

Objectives of the present disclosure are not limited to the above-mentioned objectives, and other objectives of the present disclosure not mentioned may be understood by the following description and may be seen more clearly by the examples of the present disclosure. In addition, the objectives of the present disclosure may be realized by means and combinations thereof indicated in the claims.

In order to achieve the above objectives, provided is an HVAC system including a sterilization unit. In one embodiment of the present disclosure, the HVAC system may include a sterilization unit located at an inner side of the HVAC system, wherein the sterilization unit may include a housing configured to envelop the outer side surface of the sterilization unit, an irradiation unit located on one side surface of the housing, and reflection units located on a plurality of surfaces on inner sides of the housing so as to face the irradiation unit.

In addition, the reflection units may include a first reflective surface to which a light ray incident from the irradiation unit is reflected first, and a second reflective surface to which the light ray reflected through the first reflective surface is re-reflected.

In addition, a curvature on a cross section of the first reflective surface may be configured to be relatively larger than a curvature on a cross section of the second reflective surface.

In addition, the first reflective surface may include a plurality of parabolic surfaces configured with the irradiation unit as a focal point.

In addition, the first reflective surface may be provided on one surface adjacent to the irradiation unit and include a plurality of surfaces facing the irradiation unit, wherein the first reflective surface may be configured such that the light ray reflected from the first reflective surface is incident on the second reflective surface provided on one surface facing the first reflective surface.

In addition, the first reflective surface and the second reflective surface may be respectively configured to have shapes corresponding to each other.

In addition, the irradiation unit may include an LED part projecting an LED light ray, a cooling part configured to perform cooling of the LED part, and a dome part configured to envelop at least a portion of the LED part.

In addition, the sterilization unit may be located at least at one position adjacent to a heater unit, a blower, or an inner air inlet.

As described above, the present disclosure can obtain following effects by the embodiment seen above and the configuration, combination, and use relationship to be described below.

The present disclosure has the effect of improving quality of air flowing along the inside of a vehicle by providing a sterilization unit that executes sterilization of the inside of an HVAC system.

In addition, the present disclosure has the effect of improving the sterilization performance of the air flowing in the housing by providing a plurality of reflection units such that a light ray projected through the irradiation unit is reflected at least twice.

In addition, the present disclosure provides the effect of preventing damage to plastics constituting the housing compared to a sterilizer that irradiates UV in an episodic manner.

BRIEF DESCRIPTION OF THE DRAWINGS

The above and other objectives, features, and other advantages of the present disclosure will be more clearly understood from the following detailed description when taken in conjunction with the accompanying drawings, in which:

FIG. 4B is a view showing an optical path of the sterilization unit, the optical path including the first reflective surface provided on one surface adjacent to the irradiation unit as the another embodiment of the present disclosure;

DETAILED DESCRIPTION

Figure 1:
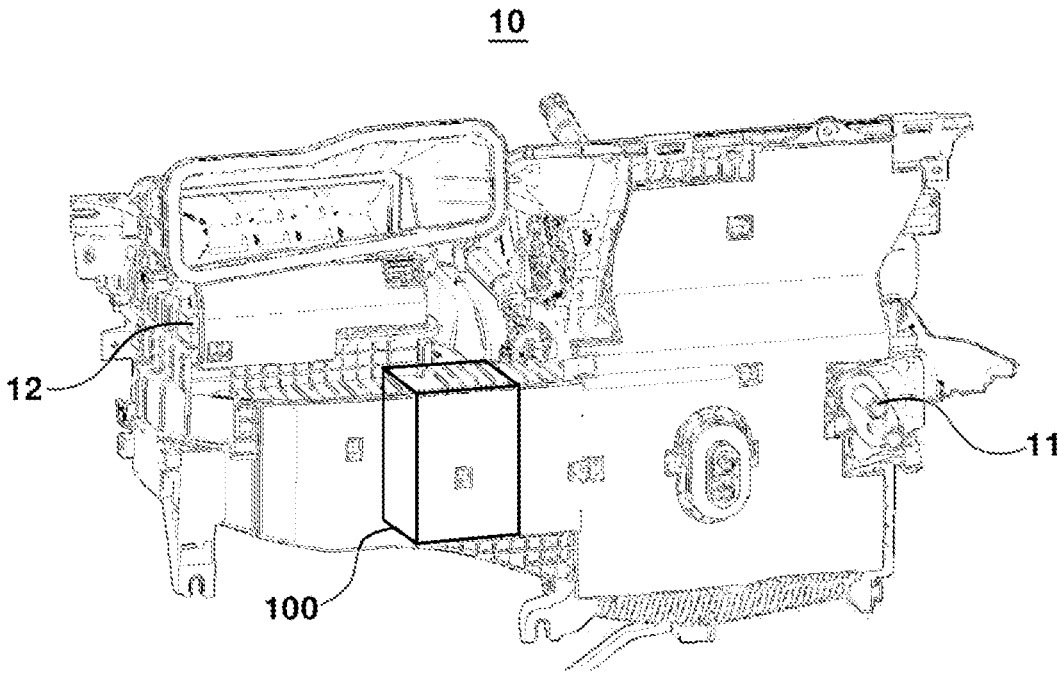
FIG. 1 is a view showing an HVAC system including a sterilization unit located between a blower and a heater unit as an embodiment of the present disclosure.

Hereinbelow, embodiments of the present disclosure will be described in more detail with reference to the accompanying drawings. The embodiments of the present disclosure may be modified in various forms, and scope of the present disclosure should not be construed as being limited to the following embodiments. The present embodiments are provided to more completely explain the present disclosure to those of ordinary skill in the art.

In addition, terms such as "part", "unit", and the like described in the specification mean a unit that processes at least one function or operation and may be implemented as hardware, software, or a combination of hardware and software.

In addition, in the present specification, the reason that the names of the components are divided into the first, the second, and the like is to distinguish the names of the components because the names of the components are the same, and the order is not necessarily limited in the following description.

Hereinafter, the embodiments will be described in detail with reference to the accompanying drawings, and in the description with reference to the accompanying drawings, the same or corresponding components are given the same reference numerals, and overlapping descriptions thereof will be omitted.

Figure 2:
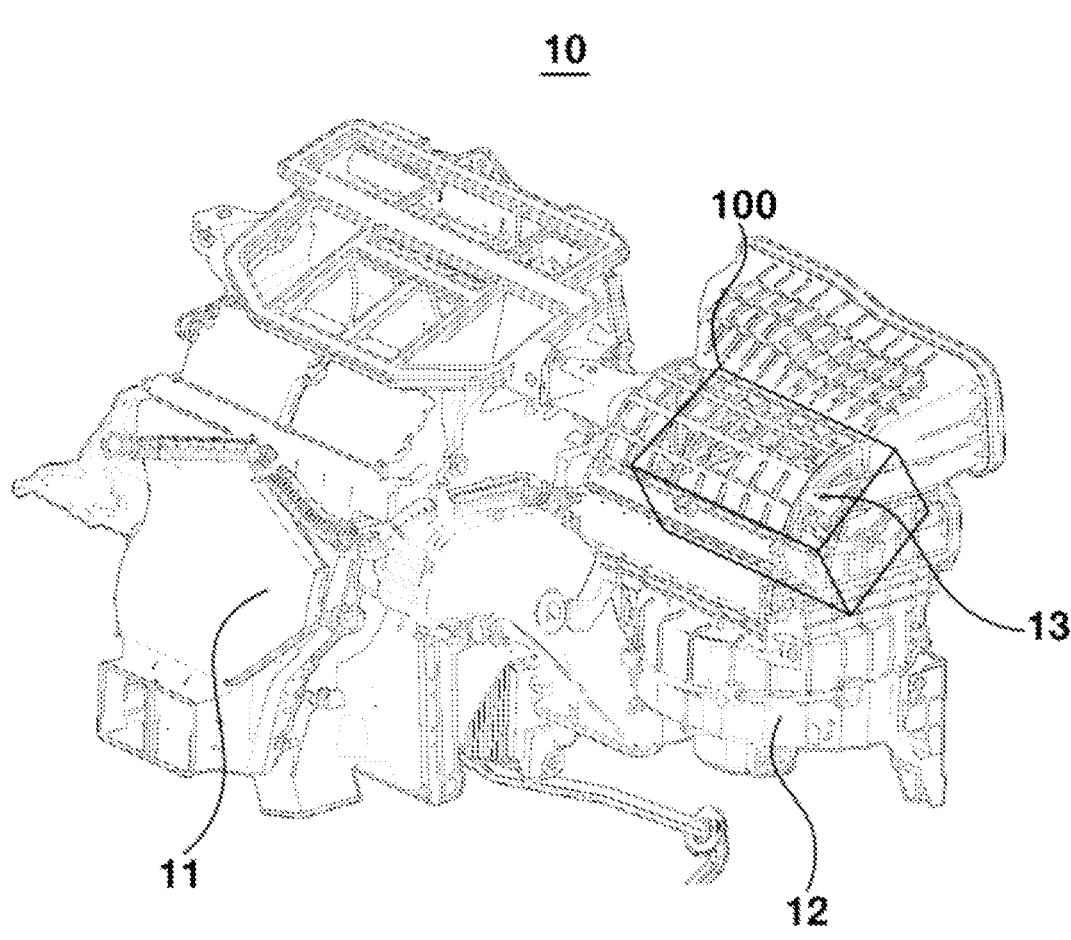
FIG. 2 is a view showing the sterilization unit configured in a position adjacent an internal/external air circulation door as the embodiment of the present disclosure.

FIGS. 1 to 2 relate to an HVAC system 10 including a sterilization unit 100 as one embodiment of the present disclosure and provide the sterilization unit 100, wherein the HVAC system 10 located in a vehicle includes at least one sterilization unit 100.

As is shown, the HVAC system 10 is a system configured to control the indoor temperature and humidity of the vehicle. Accordingly, the HVAC system 10 is configured such that the outside air introduced thereinto passes through the heater core, the blower 12, or the like to obtain the temperature and humidity that had been set in a controller, thereby being discharged to an interior of the vehicle.

In the HVAC system 10, the heater unit 11 and the blower 12 may be configured in a typical separated manner; that is, may be configured such that the blower 12 is located in a power electric (PE) room as in an electric vehicle and the heater unit 11 is located in a cabin room of the vehicle.

The sterilization unit 100 may be located adjacent to the heater unit 11, the blower 12, or an inner air inlet 13 and may be provided in the middle of the flow path of the air flowing into the HVAC or the flow path discharged into the interior of the vehicle.

FIG. 1 is a typical HVAC system 10 and is configured to have the sterilization unit located between the heater unit 11 and the blower 12. Here, the sterilization unit 100 may be configured to be located at a rear end of the blower 12 so as to execute sterilization of the air introduced from the outside.

In comparison with this, FIG. 2 includes a sterilization unit 100 provided in a position adjacent to the internal/external air circulation door. That is, it is configured to sterilize the air flowing into the inner side of the HVAC system 10 through the sterilization unit 100 provided at a position where the indoor air of the vehicle flows into the HVAC system 10.

As such, In FIGS. 1 and 2, positions of the sterilization unit 100 capable of sterilizing the air introduced into the HVAC system 10 are each shown.

Figure 3A:
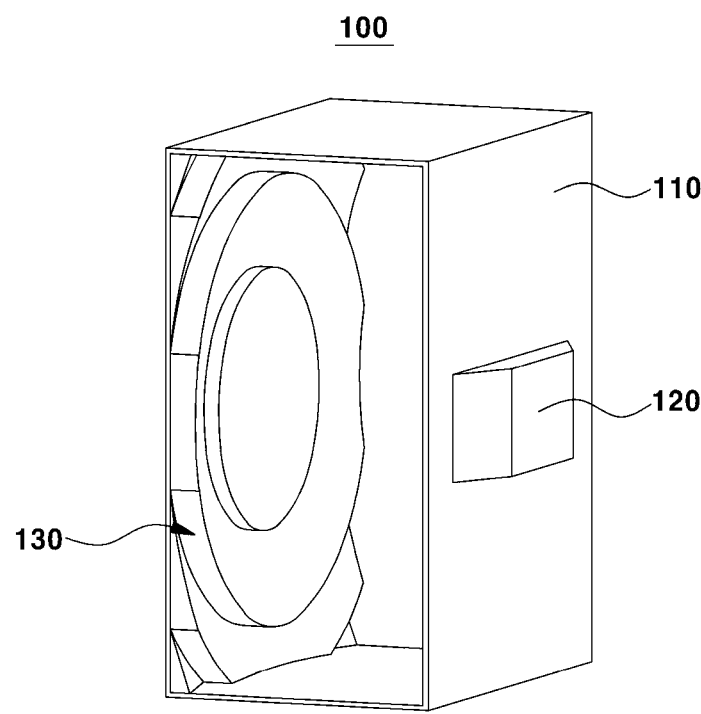
FIG. 3A is a view showing a sterilization unit including a first reflective surface facing an irradiation unit as the embodiment of the present disclosure.
Figure 3B:
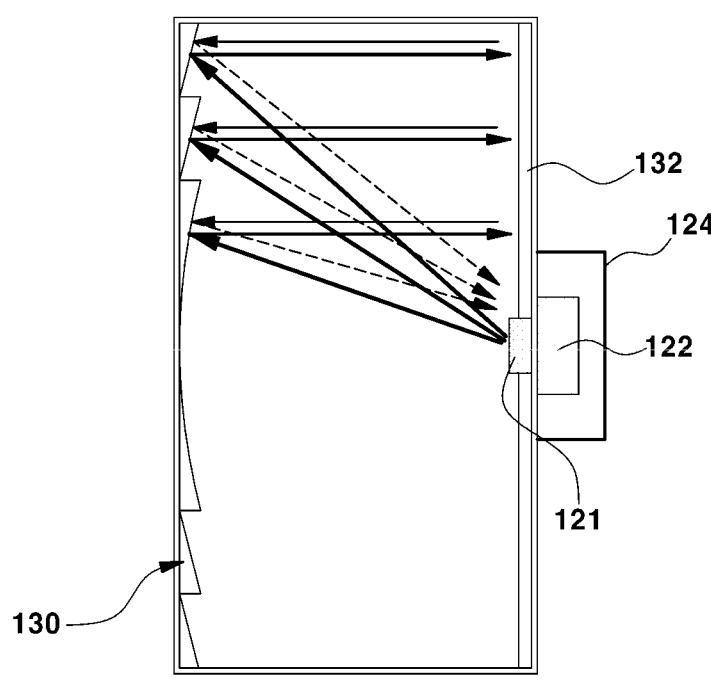
FIG. 3B is a view showing an optical path of the sterilization unit, the optical path including the first reflective surface facing the irradiation unit as the embodiment of the present disclosure.
Figure 3C:
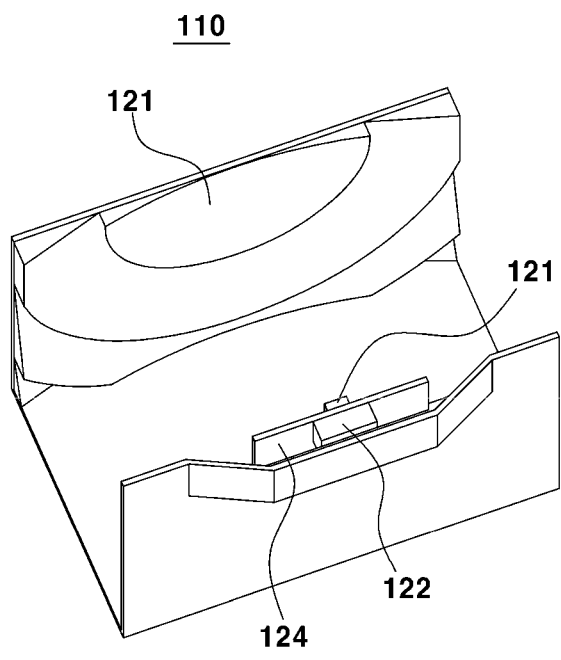
FIG. 3C is a view showing a configuration of a bypass flow path located in the irradiation unit as the embodiment of the present disclosure.

FIGS. 3A to 3C are perspective views showing the sterilization unit 100, as the embodiment of the present disclosure.

As is shown, the sterilization unit 100 includes a housing 110 and further includes an irradiation unit 120 located on one side of the housing 110. Reflection units 130 are configured to reflect a light ray incident from the irradiation unit 120 to the inside of the housing 110 to so that the light ray is reflected no less than a predetermined number of times.

Here, the reflection units 130 may be configured to face each other in a width direction of the housing 110, or the reflection units 130 may be configured to face each other in a height direction of the housing 110.

The reflection units 130 of the present disclosure may be configured to be located on at least one surface of the housing 110 and may be composed of a plurality of ellipsoidal surfaces provided with the irradiation unit 120 as a focal point so that the height of the reflection units 130 located in the housing 110 may be minimized. Accordingly, the present disclosure having the reflection units 130 having a low height provides an effect that the resistance of the airflow passing around the housing 110 is minimized.

The housing 110 is configured to provide a cross section in a rectangular shape and includes a first reflective surface 131 on an inner surface of the housing 110 facing the irradiation unit 120 and a second reflective surface 132 at a position facing the first reflective surface 131. Here, in the embodiment of the present disclosure, one surface of the inner side of the housing 110, provided with the second reflective surface 132 thereon, may be configured as one surface on which the irradiation unit 120 is located.

The irradiation unit 120 includes an LED unit 121 configured to project the light ray, a cooling unit 122 located on a rear surface of the LED unit 121 and configured to reduce heat generation of the LED unit 121 due to projection of the light ray, and a dome part 123 located on an inner side surface, adjacent to the LED unit 121 to which the light ray is incident, of the housing 110.

The cooling unit 122 may be composed of a bypass flow path 124 branched off from a main flow path of the HVAC system and may protrude to an outer surface of the housing 110, thereby being provided by being adjacent to the rear surface of the LED unit 121. As is shown in FIG. 3C, the bypass flow path 124 may be configured in a shape of protruding to the outer side of the housing 110 and, in a state in which one side of the housing 110 is opened, may be configured to allow the air to flow to an opposite side of the housing 110 along the rear surface of the LED unit 121. Accordingly, some of the air flowing along the inner side of the housing may move along the bypass flow path 124 provided on the rear surface of the LED unit 121.

In the embodiment of the present disclosure, the LED unit 121 is configured to be provided at a position facing the first reflective surface 131 and, therefore, may be configured to be located at a center of a right side surface of the housing 110 in the cross section of FIG. 3B.

The dome part 123 is configured in various shapes and is configured to execute re-reflection of the light ray so that the light ray flowing into the irradiation unit 120 is incident to the reflection units 130.

The light ray projected from the LED unit 121 is a visible sterilizing light ray in a region of a 400 nm to 410 nm (in one example, the region may be 405 nm) and is to inactivate bacteria present in an area inside the housing 110, the area being irradiated with the visible sterilizing light ray. Here, the bacteria comprise *Staphylococcus*, CONS, *Streptococcus*, Enterococci, *Clostridium*, and the like that are to be killed. When these bacteria are irradiated with visible sterilizing light ray in the above region, the bacteria are inactivated, wherein the inactivation means that the bacteria are killed or damaged in order for replication of bacteria to be reduced or prevented. In other words, exposing such bacteria to the light ray (blue light ray) having a wavelength in the above-described region stimulates an inactivation process. Using the light ray in the visible light ray region may induce inactivation of bacteria without adversely affecting human or animal health.

However, the wavelength of the light ray projected from the LED unit 121 is not limited to the visible sterilizing light ray, and the wavelength band of the light ray may be varied as needed.

The first reflective surface 131 is provided on one surface of the housing 110, the one surface being configured to face the irradiation unit 120, and thus may be composed of surfaces of ellipsoids each provided with the LED unit 121 of the irradiation unit 120 as a reference. That is, as is shown in FIG. 3B, on a side cross section, the irradiation unit 120 is composed of one focal point close to the first reflective surface 131 providing ellipsoids, and the first reflective surface 131 is provided as a portion of the ellipsoids provided with the irradiation unit 120 as the focal point. As is shown, in the embodiment of the present disclosure, the surfaces constituting the four ellipsoids may be located with the irradiation unit 120 as the focal point.

A second reflective surface 132 is located on the inner side surface, facing the first reflective surface 131, of the housing 110, so the second reflective surface 132 is located on one surface including the irradiation unit 120 and is configured in a shape parallel to the one surface of the inner side of the housing 110.

The light ray incident from the irradiation unit 120 to the first reflective surface 131 provided with the irradiation unit 120 as the focal point is configured to be reflected along a horizontal direction of the housing 110, so the reflected light ray is configured to be projected to the second reflective surface 132.

In addition, the light ray reflected along the second reflective surface 132 is configured to head the first reflective surface 131, and then the light ray re-reflected on the first reflective surface 131 is configured to have a path facing the irradiation unit 120.

Furthermore, the light ray reflected into the path facing the irradiation unit 120 is configured such that the light ray is reflected back toward the first reflective surface 131 by the dome 123 located adjacent the irradiation unit 120.

As such, the light ray incident along the first reflective surface 131 through the LED unit 121 of the irradiation unit 120 is reflected by each of the first reflective surface 131, the second reflective surface 132, and the dome 123 and is configured to be reflected at least five times when in accordance with the embodiment of the present disclosure.

Furthermore, when compared with the incoming light ray, the light ray reflected through each reflective surface is configured to maintain 70% of the energy of the incoming light ray.

Accordingly, at the inside of the housing 110 where the reflections are performed five times as in the embodiment of the present disclosure, the last reflected light ray may be configured to contain about 17% of the energy as compared to the first reflected light ray.

Figure 4A:
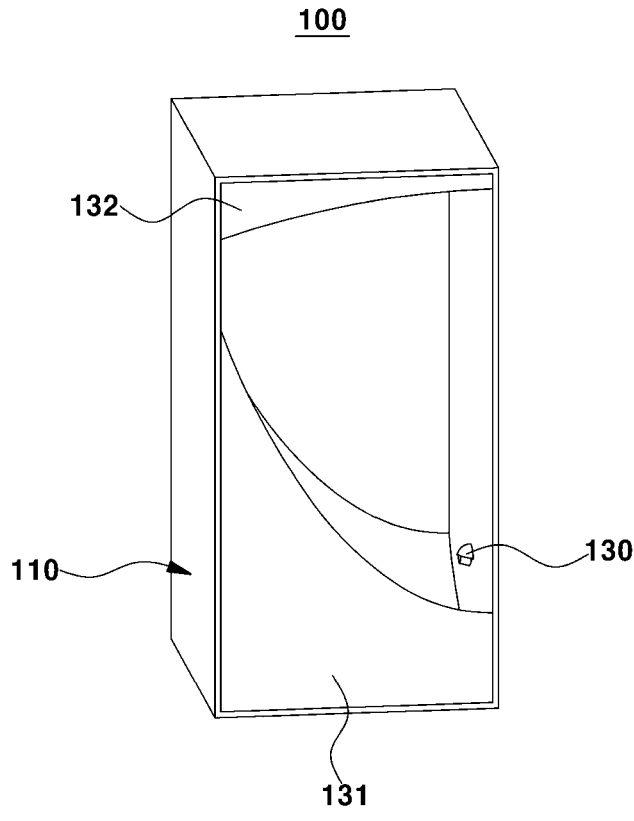
FIG. 4A is a view showing a sterilization unit including a first reflective surface provided on one surface adjacent to an irradiation unit as another embodiment of the present disclosure.
Figure 4B:
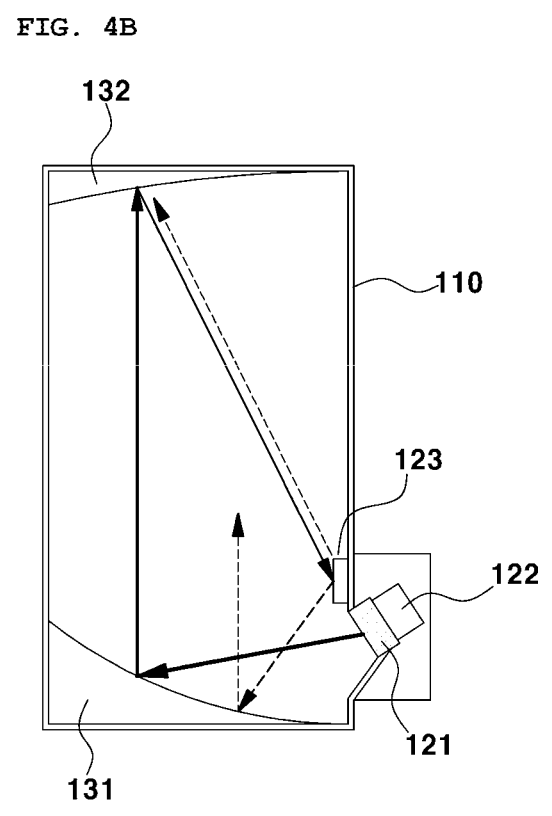

FIGS. 4A to 4B are views, as another embodiment of the present disclosure, showing a sterilization unit 100 including an irradiation unit 120 located by being biased to one side to a height direction of one surface of the inner side of the housing 110, a first reflective surface 131 located on one surface close to the irradiation unit 120 in the height direction, and a second reflective surface 132 provided at a position facing the first reflective surface 131.

The irradiation unit 120 is located on one surface having a long length in a cross section of the housing 110 and is configured to be provided in a position close to a lower end in the height direction. Moreover, the first reflective surface 131 is configured to be located on one surface, adjacent to the irradiation unit 120, of the housing 110.

The second reflective surface 132 is provided on the inner surface of the housing 110 facing the first reflective surface 131 and, more practically, as is shown, the first reflective surface 131 and the second reflective surface 132 may be provided respectively on surfaces constituting the short surfaces of the housing 110 and facing each other.

The first reflective surface 131 is provided as a single surface having a curvature in the cross section, and the second reflective surface 132 corresponding to the first reflective surface 131 is also located to correspond at a single surface having a curvature in cross section.

As is shown, curvature on a cross section of the first reflective surface 131 is configured to be relatively larger than curvature on a cross section of the second reflective surface 132. Accordingly, the light ray projected into the inner side of the housing 110 through the irradiation unit 120 is incident along the first reflective surface 131, and the light ray reflected by the first reflective surface 131 is configured to be incident to the second reflective surface 132. Furthermore, as is shown in FIG. 4B, the light ray reflected along the second reflective surface 132 is incident to a position facing the dome unit 123 configured in a position adjacent to the irradiation unit 120, and the light ray reflected on the dome unit 123 is configured to be re-incident to the first reflective surface 131.

Accordingly, the light ray incident first through the irradiation unit 120 is configured to be reflected sequentially along the first reflective surface 131, the second reflective surface 132, the dome part 123, the first reflective surface 131, and the second reflective surface 132. Through this, it is configured such that the light ray having been incident is reflected on the inner side of the housing 110 at least five times.

In the embodiment of the present disclosure, the LED unit 121 as the irradiation unit 120 is located on one surface adjacent to one end of the housing 110, thereby being configured to project the light ray therefrom. Furthermore, the LED unit 121 is provided at a position close to the one end, adjacent to the first reflective surface 131, of the housing 110, thereby being configured to make an incident angle be set to have a predetermined angle with the first reflective surface 131.

Figure 5A:
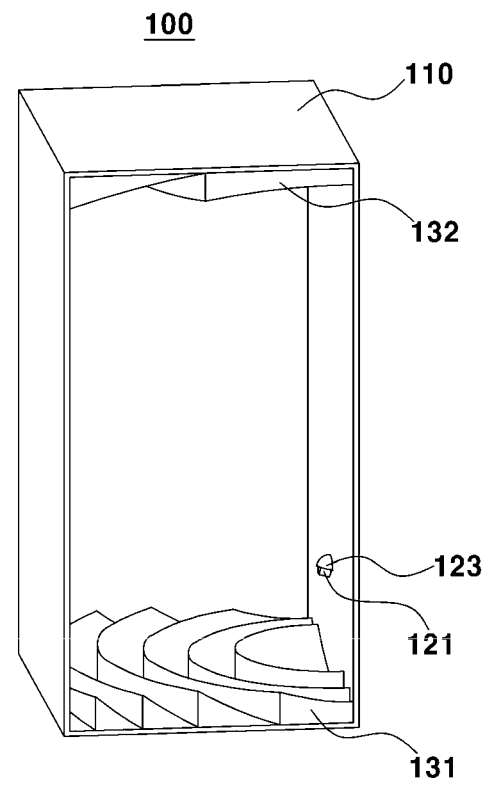
FIG. 5A is a view showing a sterilization unit including a first reflective surface provided on one surface adjacent to an irradiation unit as still another embodiment of the present disclosure.
Figure 5B:
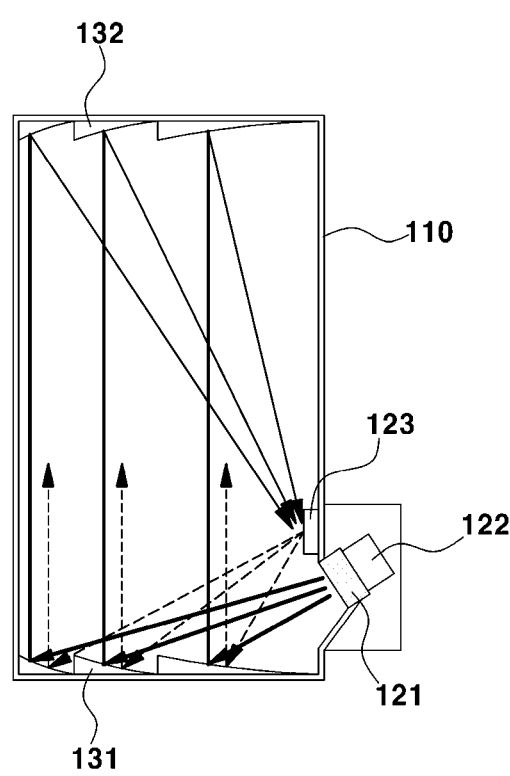
FIG. 5B is a view showing an optical path of the sterilization unit, the optical path including the first reflective surface provided on one surface adjacent to the irradiation unit as the still another embodiment of the present disclosure.

FIGS. 5A and 5B show the sterilization unit 100 including an irradiation unit 120 located at a lower end in a height direction on one surface of the housing 110 as yet another embodiment of the present disclosure.

As is shown, the irradiation unit 120 is configured to be located at a lower end of one surface of the housing 110 of the sterilization unit 100. Furthermore, the sterilization unit 100 includes a dome part 123 located on a side above LED part 121 of the irradiation part 120 of the housing 110 by being adjacent to the LED part 121.

The irradiation unit 120 is located on one surface of the housing 110 and is configured to be located at a relatively lower end in the height direction. A first reflective surface 131 configured to reflect the light ray projected from the irradiation unit 120 first is configured on a lower surface located adjacent the irradiation unit 120. Moreover, a second reflective surface 132 is configured on an upper surface facing the first reflective surface 131.

The first reflective surface 131 is configured to have a predetermined angle such that the light ray incident from the LED unit 121 is reflected and faces the second reflective surface 132. At this time, the light ray reflected on the first reflective surface 131 may be configured to be incident to the second reflective surface 132 in parallel along the height direction of the housing 110. Furthermore, the first reflective surface 131 is configured to include a plurality of surfaces configured to face the irradiation unit 120.

The second reflective surface 132 may be configured to have a shape corresponding to that of the first reflective surface 131 is configured such that the light ray incident from the first reflective surface 131 is re-reflected to irradiate the dome part 123 of the irradiation unit 120 therewith.

The dome part 123 is configured such that the light ray incident to the dome part 123 is reflected to be introduced into the first reflective surface 131, and the light ray incident to the second reflective surface 132 through the first reflective surface 131 flows into the dome part 123. That is, in the present disclosure, it is configured such that the light ray incident to the inside of the housing 110 through the LED unit 121 is re-incident to the first reflective surface 131, the second reflective surface 132, the dome part 123, the first reflective surface 131, and the second reflective surface 132, thereby executing sterilization of the air flowing inside the housing 110.

The above detailed description is illustrative of the present disclosure. In addition, the above description shows and describes exemplary implementation forms of the present disclosure, and the present disclosure may be used in various other combinations, modifications, and environments. That is, changes or modifications are possible within the scope of the concept of the disclosure disclosed herein, the scope equivalent to the described disclosure, and/or the scope of skill or knowledge in the art. The described embodiments describe the best state for implementing the technical idea of the present disclosure, and various changes required in specific application fields and uses of the present disclosure are also possible. Therefore, the detailed description of the present disclosure is not intended to limit the present disclosure to the disclosed implementation states. In addition, the accompanying claims should be construed as including other implementation states.

What is claimed is:

1. An HVAC system including a sterilization unit, the HVAC system comprising:
   an air sterilization unit located within the HVAC system, wherein the air sterilization unit includes:
   a housing configured to envelop an outer side surface of the air sterilization unit;
   an irradiation unit located on a side surface of the housing; and
   each reflection unit of a plurality of reflection units is located on at least one inner side surface of the housing to face the irradiation unit,
   wherein the plurality of reflection units comprise a plurality of ellipsoidal surfaces provided with the irradiation unit as a focal point.

2. The HVAC system of claim 1, wherein the reflection units comprise:
   a first reflective unit to which a light ray incident from the irradiation unit is reflected first; and
   a second reflective unit to which the light ray reflected through a first reflective surface is re-reflected.

3. The HVAC system of claim 2, wherein a curvature on a cross section of the first reflective unit is configured to be relatively larger than a curvature on a cross section of the second reflective unit.

4. The HVAC system of claim 2, wherein the first reflective unit comprises the plurality of ellipsoidal surfaces facing the irradiation unit, wherein the first reflective unit is configured such that the light ray reflected from the first reflective unit is incident on the second reflective unit provided on a surface facing the first reflective surface.

5. The HVAC system of claim 4, wherein the first reflective surface has a shape corresponding to a second reflective surface.

6. The HVAC system of claim 1, wherein the irradiation unit comprises:

an LED portion projecting an LED light ray;

a cooling part configured to perform cooling of the LED portion; and a dome part configured to envelop at least a portion of the LED portion.

7. The HVAC system of claim 6, wherein the dome part is configured to allow the light ray incident to the LED portion to be re-reflected to at least one reflection unit of the plurality of reflection units.

8. The HVAC system of claim 1, wherein the air sterilization unit is located at least at one position adjacent to a heater unit, a blower, or an inner air inlet.

\* \* \* \* \*